(12) United States Patent
Li et al.

(10) Patent No.: US 10,943,699 B2
(45) Date of Patent: Mar. 9, 2021

(54) SYSTEMS AND METHODS FOR IMAGE PROCESSING

(71) Applicant: SHANGHAI UNITED IMAGING HEALTHCARE CO., LTD., Shanghai (CN)

(72) Inventors: Yang Li, Shanghai (CN); Chunlin Zhao, Shanghai (CN); Wenjun Yu, Shanghai (CN); Ce Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 53 days.

(21) Appl. No.: 16/382,149

(22) Filed: Apr. 11, 2019

(65) Prior Publication Data

US 2019/0318828 A1    Oct. 17, 2019

(30) Foreign Application Priority Data

Apr. 11, 2018 (CN) .......................... 201810322914.8

(51) Int. Cl.
| | |
|---|---|
| G16H 50/20 | (2018.01) |
| G16H 30/20 | (2018.01) |
| G16H 30/40 | (2018.01) |
| G06T 15/20 | (2011.01) |
| G06N 20/00 | (2019.01) |
| G06T 7/00 | (2017.01) |

(52) U.S. Cl.
CPC ............ *G16H 50/20* (2018.01); *G06N 20/00* (2019.01); *G06T 7/0014* (2013.01); *G06T 15/205* (2013.01); *G16H 30/20* (2018.01); *G16H 30/40* (2018.01); *G06T 2207/30008* (2013.01); *G06T 2215/06* (2013.01)

(58) Field of Classification Search
CPC combination set(s) only.
See application file for complete search history.

(56) References Cited

U.S. PATENT DOCUMENTS

| | | |
|---|---|---|
| 2003/0215120 A1 | 11/2003 | Uppaluri et al. |
| 2008/0031507 A1 | 2/2008 | Uppaluri et al. |

(Continued)

FOREIGN PATENT DOCUMENTS

| | | |
|---|---|---|
| CN | 104799924 A | 7/2015 |
| CN | 107599412 A | 1/2018 |

OTHER PUBLICATIONS

Anu TC, Mallikarjunaswanny, "Detection of Bone Fracture using Image Processing Methods", International Journal of Computer Applications (0975-8887), 2015, pp. 6-9.*

(Continued)

*Primary Examiner* — Omar S Ismail
(74) *Attorney, Agent, or Firm* — Metis IP LLC

(57) ABSTRACT

The present disclosure provides computer-aided diagnosis systems and methods for detecting bone fracture. The method may include obtaining one or more medical images related to one or more bones. The method may also include obtaining a fracture detection model generated based on a machine learning model. The method may also include detecting, for at least one of the one or more medical images, one or more bone fracture regions of the one or more bones in the medical image using the fracture detection model.

20 Claims, 14 Drawing Sheets

(56) References Cited

U.S. PATENT DOCUMENTS

| | | | |
|---|---|---|---|
| 2009/0262998 A1 | 10/2009 | Wang et al. | |
| 2012/0143037 A1* | 6/2012 | Najarian | G06T 7/11 |
| | | | 600/407 |
| 2014/0233820 A1* | 8/2014 | Wu | A61B 6/5211 |
| | | | 382/131 |
| 2018/0060512 A1* | 3/2018 | Sorenson | G06K 9/46 |
| 2019/0021677 A1* | 1/2019 | Grbic | G06T 7/11 |

OTHER PUBLICATIONS

D.H Kim ,"Artificial intelligence in fracture detection: Transfer learning from deep convolutional neural networks", Clinical Radiology, vol. 73, Issue 5, May 2018, pp. 439-444, Received May 28, 2017, Accepted Nov. 14, 2017, Available online Dec. 18, 2017. , pp. 439-444.*

Robert Lindsey,"Deep neural network improves fracture detection by clinicians",PNAS, Nov. 6, 2018,vol. 115,No. 45,pp. 11591-11594.*

Helmut Ringl,"The ribs unfolded—a CT visualization algorithm for fast detection of rib fractures: effect on sensitivity and specificity in trauma patients",Emergency Radiology,European Society of Radiology 2015,Published online: Feb. 14, 2015,pp. 1867-1872.*

The Extended European Search Report in European Application No. 19168808.4 dated Nov. 8, 2019, 15 pages.

Helmut Ringl et al., The Ribs Unfolded—a CT Visualization Algorithm for Fast Detection of Rib Fractures: Effect on Sensitivity and Specificity in Trauma Patients, European Radiology, 25(7): 1865-1874, 2015.

The Partial European Search Report in European Application No. 19168808.4 dated Aug. 13, 2019, 11 pages.

Holger R. Roth et al., Deep Convolutional Networks for Automated Detection of Posterior-element Fractures on Spine CT, SPIE—The International Society for Optical Engineering, 9785 (97850P): 1-7, 2016.

Shusil Dangi et al., Cine Cardiac MRI Slice Misalignment Correction towards Full 3D Left Ventricle Segmentation, SPIE—The International Society for Optical Engineering, 10576(6): 1-13, 2018.

* cited by examiner

SYSTEMS AND METHODS FOR IMAGE PROCESSING

CROSS-REFERENCE TO RELATED APPLICATIONS

This application claims priority to Chinese Patent Application No. 201810322914.8 filed on Apr. 11, 2018, the contents of which are hereby incorporated by reference.

TECHNICAL FIELD

The present disclosure generally relates to medical imaging, and in particular, to systems and methods for bone fracture detection by way of image processing.

BACKGROUND

With the rapid development of industry and transportation, industrial injuries and injuries caused by traffic accidents, such as bone fracture, are increasing. Fracture detection and diagnosis play an important role in current medical treatment. In the existing medical treatment, doctors usually use, for example, computed tomography (CT) to detect the bone fracture. During the process of fracture detection, doctors need to observe and analyze a plurality of CT images to identify bone fracture based on the experience of the doctor. For example, in the fracture detection of ribs, due to the complicated anatomical shape of the ribs, doctors need to observe and analyze a plurality of CT images to identify bone fracture in each rib. Some bone fractures exist in positions of the ribs that are not easily observed. In this case, the doctors need to study and analyze a plurality of CT images, which rely on the experience of the doctors, and make the fracture detection laborious and subjective. Therefore, it is desirable to provide systems and/or methods for automated bone fracture detection to improve the efficiency and the accuracy of bone fracture detection.

SUMMARY

According to a first aspect of the present disclosure, a computer aided diagnosis system for bone fracture detection may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain one or more medical images related to one or more bones. The one or more processors may obtain a fracture detection model generated based on a machine learning model. The one or more processors may detect, for at least one of the one or more medical images, one or more bone fracture regions of the one or more bones in the medical image using the fracture detection model.

In some embodiments, the fracture detection model may be obtained by performing operations including: obtaining training images in which bone fractures are marked; and determining the fracture detection model by training a preliminary model using the training images.

In some embodiments, to detect the one or more bone fracture regions of the one or more bones in the medical image using the fracture detection model, the one or more processors may detect one or more candidate fracture regions in the medical image using the fracture detection model. The one or more processors may obtain the one or more bone fracture regions by removing one or more false positive regions from the one or more candidate fracture regions using a bone mask related to the one or more bones.

In some embodiments, the one or more processors may display a marker of the one or more bone fracture regions in the at least one of the one or more medical images.

In some embodiments, the one or more processors may determine a type of bone fracture in the one or more bone fracture regions using the fracture detection model.

In some embodiments, the one or more medical images may include multiple medical images taken at different slices of the one or more bones. The one or more processors may determine whether there are at least two of the multiple medical images in each of which the one or more bone fracture regions are detected. The one or more processors may determine a distance between the detected bone fracture regions in the at least two of the multiple medical images in response to a determination that there are at least two of the multiple medical images in each of which the one or more bone fracture regions are detected. The one or more processors may determine whether the distance is less than a distance threshold. The one or more processors may combine the detected bone fracture regions in the at least two of the multiple medical images in response to a determination that the distance is less than the distance threshold. The detected bone fracture regions in the at least two of the multiple medical images may be deemed to relate to a same bone fracture.

In some embodiments, the one or more processors may reconstruct one or more bone images based on the one or more detected bone fracture regions or the combined bone fracture region. The one or more processors may display a marker of the one or more detected bone fracture regions or the combined bone fracture region in the one or more bone images.

In some embodiments, the one or more bone images may include at least one of a curved planar reconstruction (CPR) image, a multiplanar reconstruction (MPR) image, and a three-dimensional (3D) rendering image.

In some embodiments, to reconstruct the CPR image, the one or more processors may extract a centerline of at least one of the one or more bones based on the one or more medical images. The one or more processors may generate a stretched CPR image based on the centerline of the bone.

In some embodiments, the one or more processors may display a management list for managing at least one of one or more bone masks related to the one or more bones and information related to the one or more detected bone fracture regions.

In some embodiments, the one or more processors may receive an instruction related to selecting at least one of the one or more bones. The instruction may be generated through the management list or the 3D rendering image. The one or more processors may display at least one of the stretched CPR image and one or more MPR images related to the at least one selected bone based on the instruction.

In some embodiments, the fracture detection model may be obtained based on a convolutional neural network (CNN).

In some embodiments, the one or more medical images may include multiple medical images. The one or more processors may receive an instruction of selecting, for display, a first location in a first medical image of the one or more medical images. The one or more processors may simultaneously display the first medical image, or a portion thereof, including the selected first location and a second medical image, or a portion thereof, of the one or more medical image. The second medical image may include a second location corresponding to the first location.

In some embodiments, the displaying of the second medical image, or a portion thereof, may include displaying a marker of the second location.

In some embodiments, the one or more processors may generate, for at least one of the one or more medical images, a target image including the one or more bones by segmenting the one or more bones from the medical image.

According to another aspect of the present disclosure, a computer aided diagnosis method for bone fracture detection may include one or more of the following operations. One or more processors may obtain one or more medical images related to one or more bones. The one or more processors may obtain a fracture detection model generated based on a machine learning model. The one or more processors may detect, for at least one of the one or more medical images, one or more bone fracture regions of the one or more bones in the medical image using the fracture detection model.

According to yet another aspect of the present disclosure, a computer aided diagnosis system for bone fracture detection may include an obtaining module configured to obtain one or more medical images related to one or more bones. The system may also include a processing module configured to obtain a fracture detection model generated based on a machine learning model and detect, for at least one of the one or more medical images, one or more bone fracture regions of the one or more bones in the medical image using the fracture detection model.

According to yet another aspect of the present disclosure, a non-transitory computer readable medium may comprise at least one set of instructions for bone fracture detection. The at least one set of instructions may be executed by one or more processors of a computer server. The one or more processors may obtain one or more medical images related to one or more bones. The one or more processors may obtain a fracture detection model generated based on a machine learning model. The one or more processors may detect, for at least one of the one or more medical images, one or more bone fracture regions of the one or more bones in the medical image using the fracture detection model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
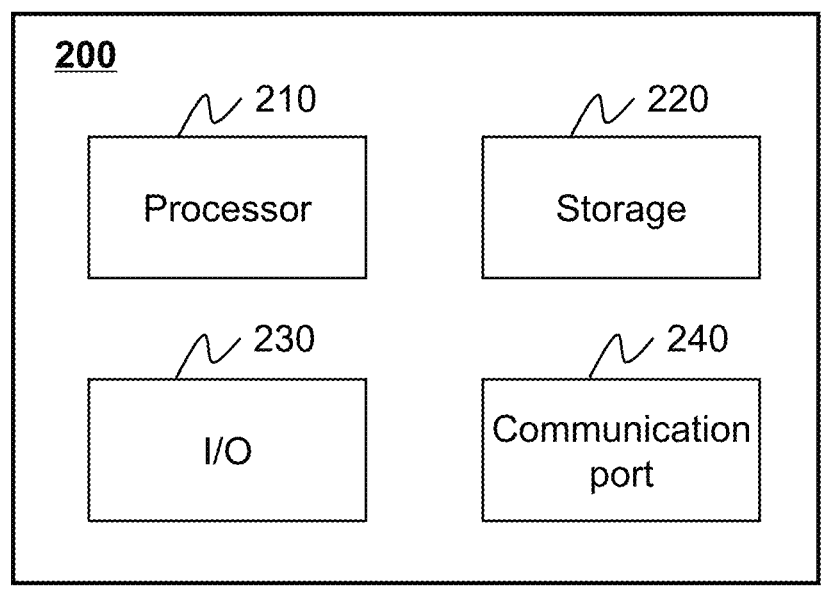
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for automated bone fracture detection by way of image processing. In the systems and methods for automated bone fracture detection in the present disclosure, bone fractures in medical images may be automatically detected using a bone fracture detection model. The fracture detection model may be developed on the basis of a machine learning model. In existing processes for fracture detection, doctors may need to analyze a plurality of medical images and use their own experience to detect bone fractures represented in the images. Compared with the existing processes for fracture detection, the methods and/or systems for fracture detection in the present disclosure may achieve automated detection using a fracture detection model, which may reduce manual operations and the time to perform the fracture detection, improve the efficiency and/or the accuracy of the fracture detection, and/or obtain a more objective fracture detection result.

In some embodiments of the present disclosure, a marker of the detected bone fracture region may be displayed in an original image generated based on raw data obtained during a scan of the bone (e.g., a rib), a curved planar reconstruction (CPR) image (e.g., a stretched CPR image), a multiplanar reconstruction (MPR) image, a three-dimensional (3D) rendering image, or the like. During the reconstruction of the stretched CPR image, a centerline of the bone may be automatically extracted based on image data (e.g., the original images of different slices of the bone), instead of being manually determined. The stretched CPR image may be reconstructed based on the centerline. In the stretched CPR image of a rib, the rib may be displayed from a view parallel to the rib (e.g., along the extending direction of the rib), which may make it relatively easy for doctors to observe the entire and real morphology of the rib in the CPR image.

Figure 1:
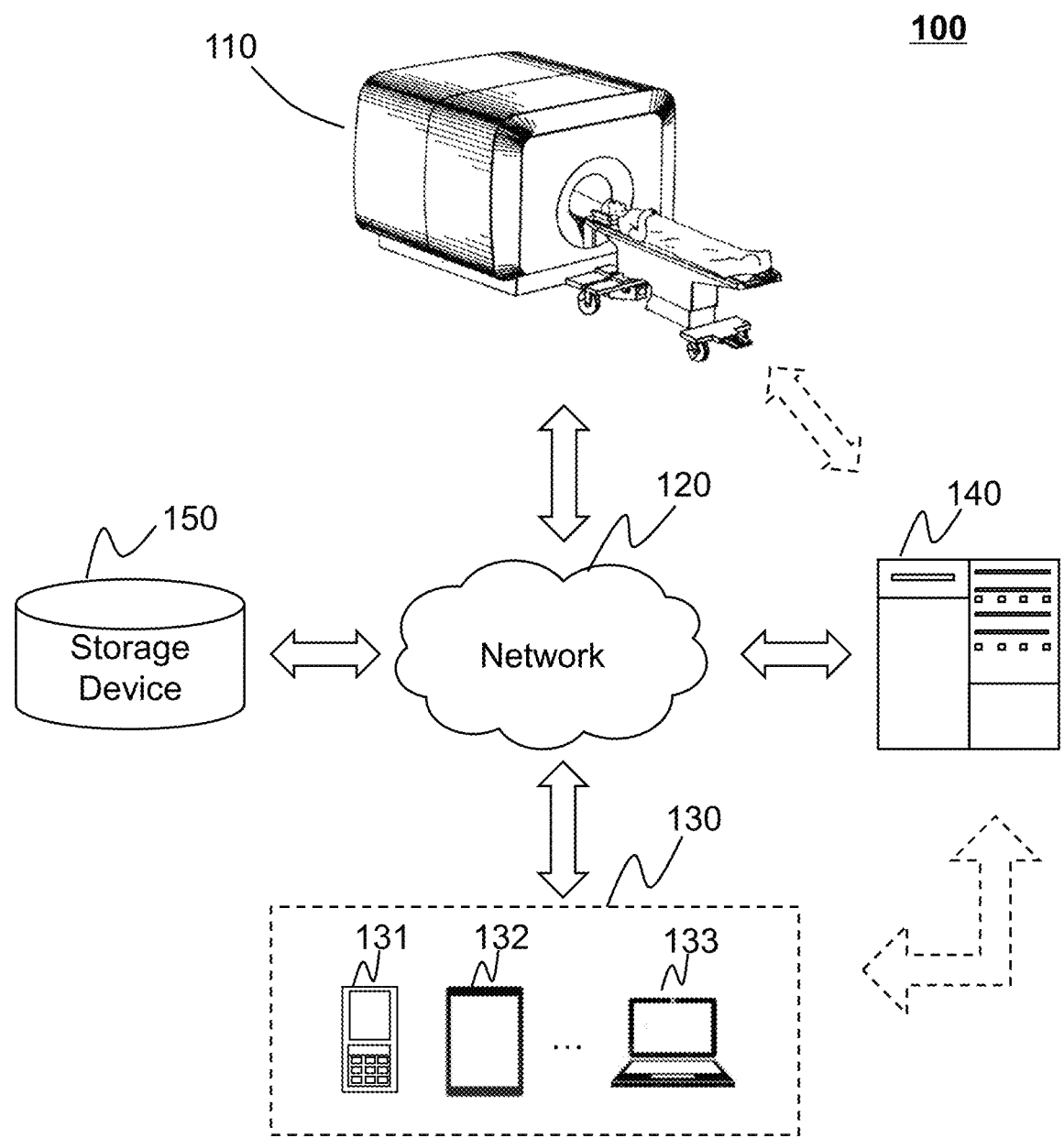
FIG. 1 is a schematic diagram illustrating an exemplary computer aided diagnosis according to some embodiments of the present disclosure.

FIG. 1 is a schematic diagram illustrating an exemplary computer aided diagnosis system 100 according to some embodiments of the present disclosure. As illustrated, the computer aided diagnosis system 100 may include an imaging device 110, a network 120, a user terminal 130, a processing device 140, and a storage device 150. The components of the computer aided diagnosis system 100 may be connected in one or more of various ways. Mere by way of example, as illustrated in FIG. 1, the imaging device 110 may be connected to the processing device 140 through the network 120. As another example, the imaging device 110 may be connected to the processing device 140 directly (as indicated by the bi-directional arrow in dotted lines linking the imaging device 110 and the processing device 140). As a further example, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the user terminal 130 and the processing device 140) or through the network 120.

The imaging device 110 may scan an object located within its detection region and generate a plurality of data relating to the object. In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, bones, or the like, or any combination thereof.

In some embodiments, the imaging device 110 may include a magnetic resonance imaging (MRI) device, a positron emission tomography (PET) device, a computed tomography (CT) device, a radiography device, or the like, or any combination thereof.

The network 120 may include any suitable network that can facilitate the exchange of information and/or data for the computer aided diagnosis system 100. In some embodiments, one or more components of the computer aided diagnosis system 100 (e.g., the imaging device 110, the user terminal 130, the processing device 140, or the storage device 150) may communicate information and/or data with one or more other components of the computer aided diagnosis system 100 via the network 120. For example, the processing device 140 may obtain raw data from the imaging device 110 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the computer aided diagnosis system 100 may be connected to the network 120 to exchange data and/or information.

The user terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the user terminal 130 may remotely operate the imaging device 110 and/or the processing device 140. In some embodiments, the user terminal 130 may operate the imaging device 110 and/or the processing device 140 via a wireless connection. In some embodiments, the user terminal 130 may receive information and/or instructions inputted by a user, and send the received information and/or instructions to the imaging device 110 or to the processing device 140 via the network 120. In some embodiments, the user terminal 130 may receive data and/or information from the processing device 140. In some embodiments, the user terminal 130 may be part of the processing device 140. In some embodiments, the user terminal 130 may be omitted.

The processing device 140 may process data and/or information obtained from the imaging device 110, the user terminal 130, and/or the storage device 150. For example, the processing device 140 may detect a bone fracture in one or more medical images by processing the one or more medical images. In some embodiments, the processing device 140 may be a single server or a server group. The server group may be centralized or distributed. In some embodiments, the processing device 140 may be local or remote. For example, the processing device 140 may access information and/or data stored in or acquired by the imaging device 110, the user terminal 130, and/or the storage device 150 via the network 120. As another example, the processing device 140 may be directly connected to the imaging device 110, the user terminal 130, and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the imaging device 110, the user terminal 130 and/or the processing device 140. For example, the storage device 150 may store one or more medical images generated by the processing device 140 based on raw data obtained from the imaging device 110. In some embodiments, the storage device 150 may store data and/or instructions that the processing device 140 may execute or use to perform exemplary methods described in the present disclosure. For example, the storage device 150 may store instructions that the processing device 140 may execute to detect bone fractures in one or more medical images by processing the one or more medical images. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the computer aided diagnosis system 100 (e.g., the imaging device 110, the processing device 140, the user terminal 130, etc.). One or more components of the computer aided diagnosis system 100 may access the data or instructions stored in the storage device 150 via the network 120. In some embodiments, the storage device 150 may be directly connected to or communicate with one or more components of the computer aided diagnosis system 100 (e.g., the imaging device 110, the processing device 140, the user terminal 130, etc.). In some embodiments, the storage device 150 may be part of the processing device 140.

FIG. 2 is a schematic diagram illustrating exemplary hardware and/or software components of a computing device on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 210 may detect bone fractures in one or more medical images by processing the one or more medical images. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors. For example, if in the present disclosure the processor of the computing device 200 executes both operations A and B, it should be understood that operations A and step B may also be performed by two different processors jointly or separately in the computing device 200 (e.g., a first processor executes operation A and a second processor executes operation B, or the first and second processors jointly execute operations A and B).

The storage 220 may store data/information obtained from the imaging device 110, the user terminal 130, the storage device 150, or any other component of the computer aided diagnosis system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 to detect bone fractures in one or more medical images by processing the one or more medical images.

The I/O 230 may input or output signals, data, or information. In some embodiments, the I/O 230 may enable a user interaction with the processing device 140. In some embodiments, the I/O 230 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

Merely by way of example, a user (e.g., an operator) of the processing device 140 may input data related to an object (e.g., a patient) that is being/to be imaged/scanned through the I/O 230. The data related to the object may include identification information (e.g., the name, age, gender, medical history, contract information, physical examination result, etc.) and/or the test information including the nature of the scan that must be performed. The user may also input parameters needed for the operation of the imaging device 110. For example, for CT imaging, the user may input a scan protocol including a scanning time, a region of interest (ROI), a rotation speed of the imaging device 110, a voltage/current intensity, etc. The I/O may also display medical images.

The communication port 240 may be connected to a network (e.g., the network 120) to facilitate data communications. The communication port 240 may establish connections between the processing device 140 and the imaging device 110, the user terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
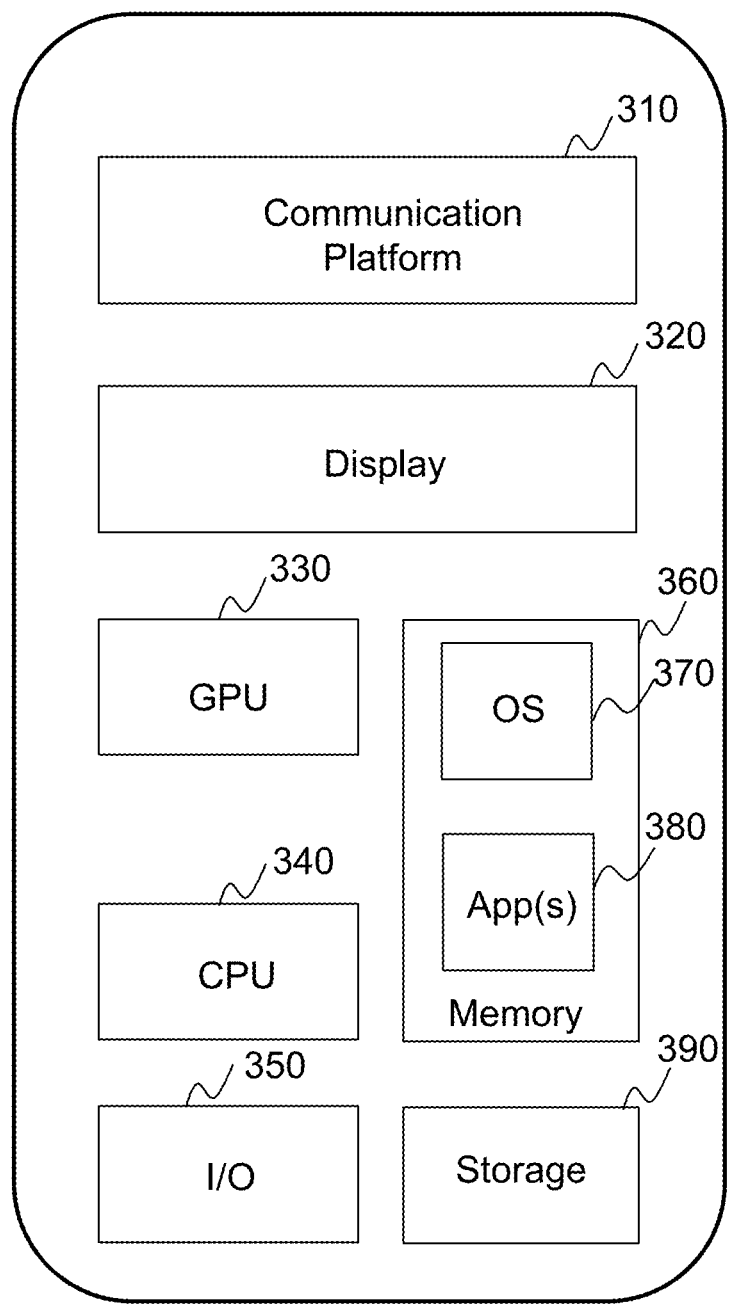
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device on which the user terminal 130 may be implemented according to some embodiments of the present disclosure. As illustrated in FIG. 3, the mobile device 300 may include a communication platform 310, a display 320, a graphics processing unit (GPU) 330, a central processing unit (CPU)

340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the computer aided diagnosis system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

For illustration purposes, the methods and/or systems for bone fracture detection in the present disclosure are described with reference to ribs as an example. It should be noted that the methods and/or systems for bone fracture detection described below are merely some examples or implementations. For persons having ordinary skills in the art, the methods and/or systems for bone fracture detection in the present disclosure may be applied to bone fracture detection of other kinds of bones, such as tibias, spine, etc.

It should be noted that, in the present disclosure, an image, or a portion thereof (e.g., a region in the image) corresponding to an object (e.g., tissue, an organ, a tumor, etc.) may be referred to as an image, or a portion of thereof (e.g., a region) of or including the object, or the object itself. For instance, a region in an image that corresponds to or represents a bone may be described as that the region includes a bone. As another example, an image of or including a bone may be referred to a bone image, or simply bone. For brevity, that a portion of an image corresponding to or representing an object is processed (e.g., extracted, segmented, etc.) may be described as the object is processed. For instance, that a portion of an image corresponding to a bone is segmented from the rest of the image may be described as that the bone is segmented from the image.

Figure 4:
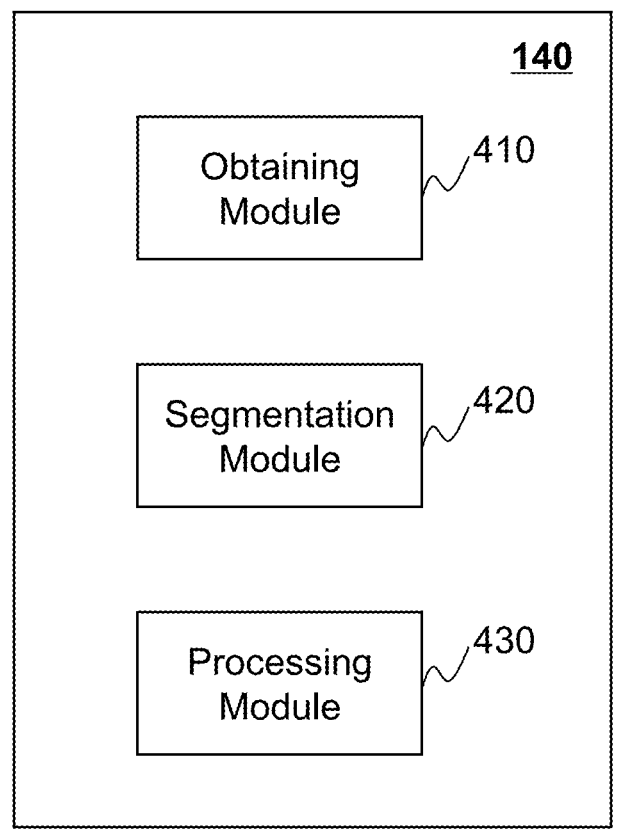
FIG. 4 is a schematic block diagram illustrating an exemplary processing device according to some embodiments of the present disclosure.

FIG. 4 is a schematic block diagram illustrating an exemplary processing device according to some embodiments of the present disclosure. The processing device 140 may include an obtaining module 410, a segmentation module 420, and a processing module 430.

The obtaining module 410 may be configured to obtain a medical image related to one or more ribs. The segmentation module 420 may be configured to generate a target image including the one or more ribs by segmenting the one or more ribs from the medical image. The processing module 430 may be configured to detect a bone fracture region of the one or more ribs in the target image using a fracture detection model.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data generated during any process performed by any component of in the processing device 140. As another example, each of components of the processing device 140 may include a storage device. Additionally or alternatively, the components of the processing device 140 may share a common storage device.

Figure 5A:
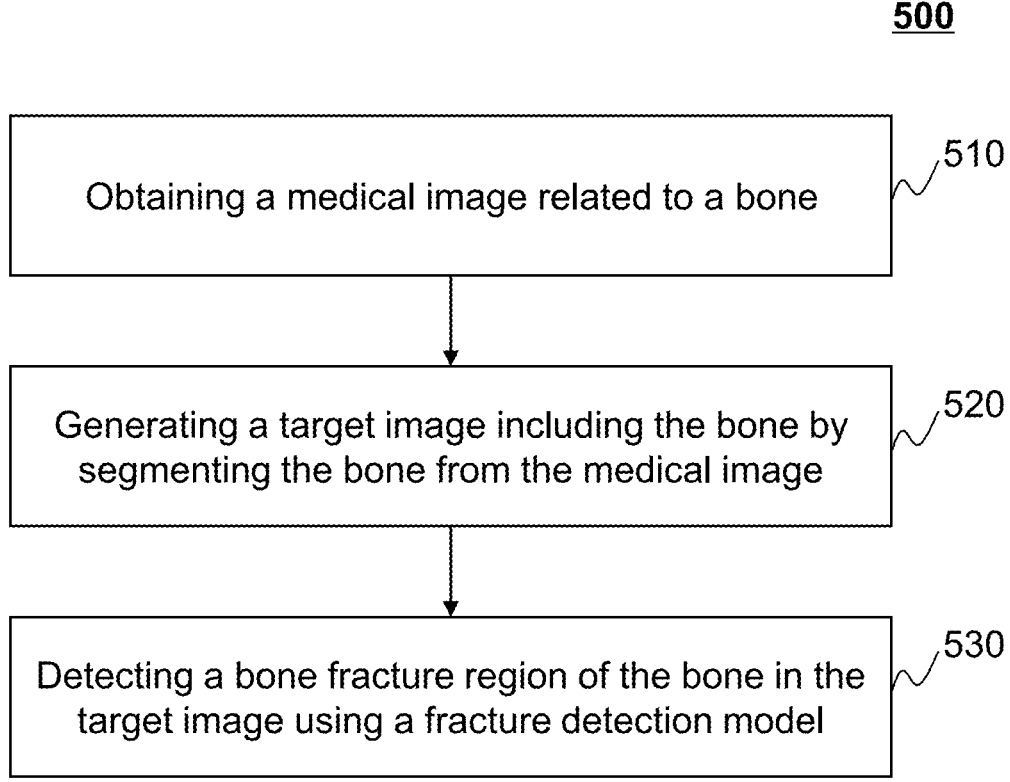
FIG. 5A is a flowchart illustrating an exemplary process for detecting bone fracture according to some embodiments of the present disclosure.

FIG. 5A is a flowchart illustrating an exemplary process for detecting bone fracture according to some embodiments of the present disclosure. In some embodiments, the process 500 may be implemented in the computer aided diagnosis system 100 illustrated in FIG. 1. For example, the process 500 may be stored in a storage medium (e.g., the storage device 150, or the storage 220 of the processing device 140) in the form of instructions, and can be invoked and/or executed by the processing device 140 (e.g., the processor 210 of the processing device 140, or one or more modules in the processing device 140 illustrated in FIG. 4). The operations of the illustrated process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 140 (e.g., the obtaining module 410) may obtain a medical image related to one or more ribs.

In some embodiments, the medical image may include a CT image, an X-ray image, an MRI image, a PET image, a multi-modality image, or the like, or any combination thereof. Exemplary multi-modality images may include a CT-MRI image, a PET-CT image, a PET-MRI image, or the like.

In some embodiments, the medical image may be an original image generated using raw data obtained from a scan process of an object using the imaging device 110. For example, the imaging device 110 may be a CT scanner. During a scan process of an object (e.g., an ROI of a patient including the ribs), an X-ray generator of the CT scanner may emit X-rays. The X-rays may pass through a cross-section (e.g., a slice) of the ROI and be received by a detector of the CT scanner. The detector may transform light signals of the X-rays into electronic signals. The electronic signals may be transformed into digital signals by an analogdigital converter (ADC). The CT scanner may transmit the digital signals to the processing device 140. The processing device 140 may process the digital signals (e.g., the raw data) to generate a CT image (e.g., the original image) of the slice.

In some embodiments, the medical image may be a reconstruction image using one or more original images (e.g., original image data). For example, the reconstruction image may be a multiplanar reconstruction (MPR) image, a curved planar reconstruction (CPR) image, a three-dimensional (3D) rendering image, or the like.

In some embodiments, the medical image may be a two-dimensional (2D) image or a three-dimensional (3D) image.

In 520, the processing device 140 (e.g., the segmentation module 420) may generate a target image including the one or more ribs by segmenting the one or more ribs from the medical image.

In some embodiments, the processing device 140 may generate a target image including all bone structures including the one or more ribs by segmenting all bone structures from the medical image. In some embodiments, the processing device 140 may generate a target image including only the one or more ribs by segmenting the one or more ribs from the medical image. For example, the medical image may include ribs, a spine, clavicles, and other non-bone tissues such as a lung. The processing device 140 may generate a target image including the ribs, the spine, and the clavicles by segmenting the ribs, the spine, and the clavicles from the medical image. Alternatively, the processing device 140 may generate a target image including only the ribs by segmenting the ribs from the medical image.

In some embodiments, the target image may be generated using any existing image segmentation technology, such as a threshold-based segmentation algorithm, an edge-based segmentation algorithm, a region-based segmentation algorithm, a clustering-based algorithm, an image segmentation algorithm based on wavelet transform, an image segmentation algorithm based on mathematical morphology, and an image segmentation algorithm based on machine learning, a tracking algorithm, or the like, or any combination thereof.

For example, the processing device 140 may determine a bone mask including the one or more ribs based on the medical image. The bone mask may be generated by extracting the one or more ribs in the medical image using any existing segmentation technology, such as a threshold-based segmentation algorithm, an edge-based segmentation algorithm, a region-based segmentation algorithm, a clustering-based algorithm, an image segmentation algorithm based on wavelet transform, an image segmentation algorithm based on mathematical morphology, and an image segmentation algorithm based on machine learning, a tracking algorithm, or the like, or any combination thereof. In some embodiments, the bone mask may be a binary image that is a digital image that has only two possible values (e.g., 1 and 0) for each pixel or voxel. Typically, the two colors used for a binary image may be black (e.g., corresponding the value of 0) and white (e.g., corresponding the value of 1). The color (e.g., white) used for the target (e.g., the one or more ribs) in the image is the foreground color while the rest of the image is the background color (e.g., black).

The processing device 140 may generate the target image using the bone mask. For example, the processing device 140 may multiply the bone mask by the medical image, that is, multiply each pixel (or voxel) value of the bone mask by the corresponding pixel (or voxel) value of the medical image. In this way, the pixel (or voxel) values of the target (e.g., the one or more ribs) in the medical image are not changed and the pixel (or voxel) values of the rest of the medical image are changed to 0, thereby generating the target image.

As another example, the processing device 140 may obtain a bone segmentation model. The processing device 140 may generate the target image by segmenting the one or more ribs from the medical image using the bone segmentation model. The bone segmentation model may be a machine learning model. Preferably, the bone segmentation model may be a deep learning model.

In 530, the processing device 140 (e.g., the processing module 430) may detect a bone fracture region of the one or more ribs in the target image using a fracture detection model. The processing device 140 may detect the bone fracture region in the target image, which is faster than detecting the bone fracture region in the medical image.

In some embodiments, the fracture detection model may be a 2D fracture detection model applicable to 2D images. In some embodiments, the fracture detection model may be a 3D fracture detection model applicable to 3D images.

In some embodiments, the fracture detection model may be generated based on a machine learning model. For instance, the fracture detection model may be a deep learning model. Merely by way of example, the fracture detection model may be a convolutional neural network (CNN), such as a visual geometry group network (VGG), residual neural network (resNet), etc.

In some embodiments, the fracture detection model and the bone segmentation model may be two different models. In some embodiments, the fracture detection model may be a model having functions of the bone fracture detection and bone segmentation.

In some embodiments, the fracture detection model may be generated by the following operations. Training images may be obtained. The training images may be images in which bone fractures are identified. In some embodiments, the fracture detection model may need to be applicable to fracture detection in different kinds of images, such as CT images, MRI images, PET images, multi-modality images, etc. In this case, the training images may include different kinds of images. In some embodiments, the fracture detection model may need to be applicable to fracture detection in a specific type of images, such as CT images. In this case, the training images may include CT images. In some embodiments, the fracture detection model may need to be applicable to fracture detection of different kinds of bones, such as ribs, tibias, etc. In this case, the training images may be images in which bone fractures are identified in different kinds of bones. In some embodiments, the fracture detection model may be required to be applicable to fracture detection of a specific kind of bones, such as ribs. In this case, the training images may be images in which bone fractures are identified in ribs. In some embodiments, the fracture detection model may need to be applicable to 2D images or 3D images. In this case, the training images may be 2D images or 3D images.

In the training images, the bone fractures may be marked. In some embodiments, the bone fractures may be marked manually. For example, the training images may be displayed and a doctor may mark the bone fractures in the training images using, for example, a mouse or a touch screen based on, for example, diagnosis reports of the training images. In some embodiments, the bone fractures may be marked automatically. For example, the training images may be input to a computing device. The computing device may automatically mark the bone fractures based on, for example, diagnosis reports of the training images. In some embodiments, a doctor may manually modify the marker of the bone fractures automatically determined by the computing device.

In some embodiments, a location of the bone fracture and/or a type of the bone fracture (e.g., such as osteophytes, displaced fractures, non-displaced fractures, abnormal cortical bones, occult fractures, etc.) may be marked. The location of the bone fracture may be marked in any form. For example, the location of bone fracture may be included in a frame (e.g., a rectangle frame, a circle frame, etc.). As another example, the location of bone fracture may be highlighted. As still another example, the location of bone fracture may be filled with different colors, etc.

In some embodiments, if the fracture detection model having functions of bone segmentation and fracture detection is desired, the region belonging to ribs may also be marked in the training images. For example, pixels (or voxels) of cortical bones and cancellous bones of ribs may be marked in the training images.

The fracture detection model may be generated by training a preliminary model using the training images.

In some embodiments, the fracture detection model may be generated by the processing device 140 or an external device communicating with the computer aided diagnosis system 100. In some embodiment, the processing device 140 may generate the fracture detection model in advance and store the fracture detection model in a storage medium (e.g., the storage device 150, the storage 220 of the processing device 140). When detecting the bone fracture region, the processing device 140 may obtain the fracture detection model from the storage medium. In some embodiments, the external device may generate the fracture detection model in advance and store the fracture detection model locally or in the storage medium (e.g., the storage device 150, the storage 220 of the processing device 140) of the computer aided diagnosis system 100. When detecting the bone fracture region, the processing device 140 may obtain the fracture detection model from the storage medium of the computer aided diagnosis system 100 or the external device.

In some embodiments, the processing device 140 may input the target image into the fracture detection model. The fracture detection model may output a fracture detection result including a determination as to whether there is a bone fracture in the target image, a location of a bone fracture region in the target image, a type of bone fracture in the bone fracture region, or the like, or any combination thereof. In some embodiments, the processing device 140 (e.g., the processing module 430) may display the fracture detection result in the target image and/or the medical image through, for example, the I/O 230 of the processing device 140. For example, the processing device 140 may display a text indicating that there is no bone fracture. As another example, the processing device 140 may display a marker of the detected bone fracture region. The marker of the detected bone fracture region may include a frame (e.g., a rectangle frame, a circle frame, etc.), a highlight, filling with different colors, a label, a file identifier, or the like, or any combination thereof. As still another example, the processing device 140 may display a text indicating the type of bone fracture in the bone fracture region.

Figure 6:
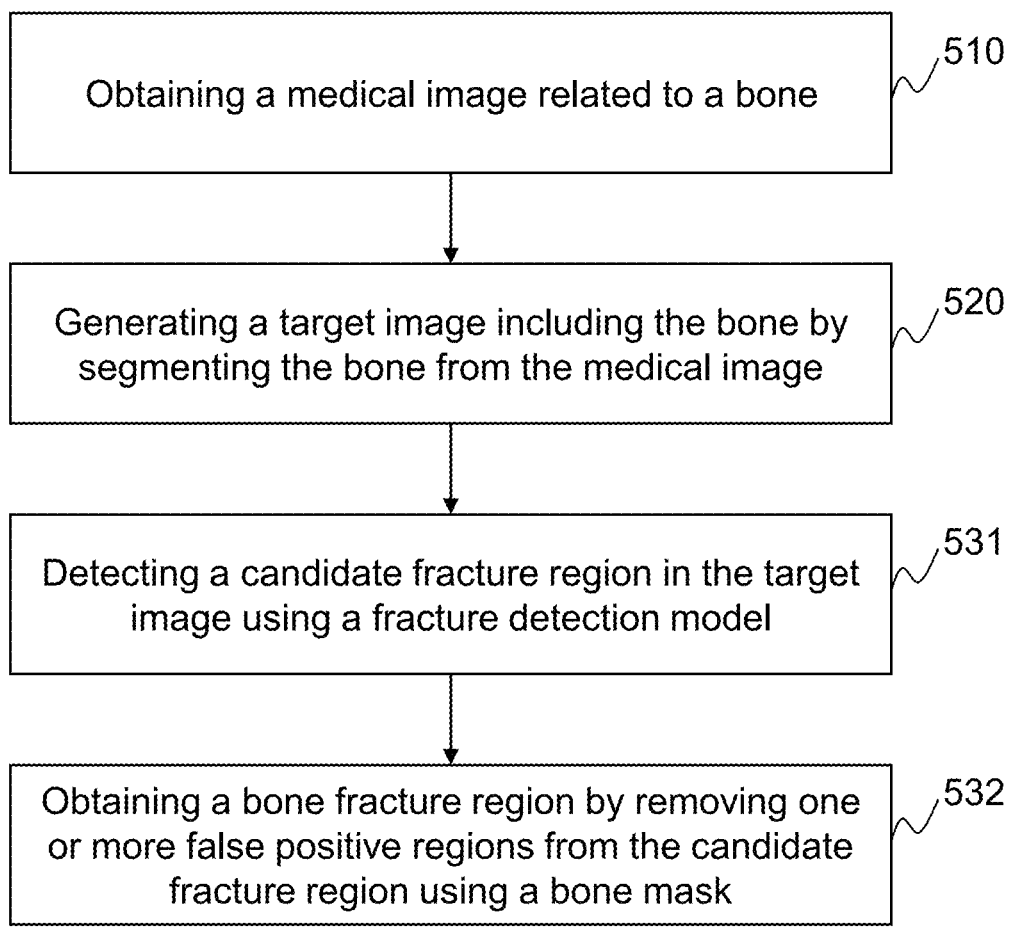
FIG. 6 is a flowchart illustrating an exemplary process for detecting bone fracture according to some embodiments of the present disclosure.

In some embodiments, operation 530 may be performed based on operations 531 and 532 in FIG. 6 showing an exemplary process 600 for detecting bone fracture according to some embodiments of the present disclosure.

In 531, the processing device 140 (e.g., the processing module 430) may detect a candidate fracture region in the target image using the fracture detection model.

In 532, the processing device 140 (e.g., the processing module 430) may obtain a bone fracture region by removing one or more false positive regions from the candidate fracture region using the bone mask. The false positive region may refer to a region that is actually not a bone fracture region but is determined as a bone fracture region by the fracture detection model. For example, the fracture detection model may determine a region including non-bone tissue and/or air as a bone fracture region. In order to avoid a false positive region in the final detection result that may mislead doctors over the diagnosis of bone fracture, the processing device 140 may remove one or more false positive regions from the candidate fracture region using the bone mask.

In some embodiments, the processing device 140 may detect bone fractures in a plurality of medical images simultaneously or one by one based on the process 500.

In some embodiments, the processing device 140 may detect bone fractures in a series of original images taken at different slices of an ROI including the ribs. For example, in order to determine whether there are one or more bone fractures in the ribs of a patient, the imaging device 110 may scan an ROI including the ribs of the patient at different cross sections (e.g., slices) of the ROI. The processing device 140 may generate a series of original images corresponding to the scanned slices. The processing device 140 may detect bone fractures in the original images.

In some embodiments, the processing device 140 may determine whether there are at least two of the original images in which the bone fracture region is detected. The processing device 140 may determine a distance between the detected bone fracture regions in the at least two of the original images in response to a determination that there are at least two of the original images in which the bone fracture region is detected. The processing device 140 may determine whether the distance is less than or equal to a distance threshold. The processing device 140 may combine the detected bone fracture regions in the at least two of the original images in response to a determination that the distance is less than or equal to the distance threshold.

Merely by way of example, the processing device 140 may detect N bone fracture regions in the original images using the fracture detection model. The processing device 140 may combine the detected fracture regions whose distance between each other that is shorter than the distance threshold, and determine M combined bone fracture regions. N and M are integers, N is greater than 1, and N is greater than or equal to M.

Merely by way of example, in the 2D medical imaging, a plurality of original images are taken at different successive slices of an ROI including the ribs. Two neighbor slices of the successive slices may represent two neighbor locations of the ROI in the space. A bone fracture in the ribs may be reflected in the original images corresponding to some neighbor slices of the successive slices. Therefore, when the 2D fracture detection model detects at least two bone fracture regions in the original images, and the detected bone fracture regions are corresponding to different slices, the processing device 140 may determine that the detected bone fracture regions with a distance between each other that is less than the distance threshold correspond to a same bone fracture, and combine the detected bone fracture regions whose distance between each other that is less than the distance threshold.

In some embodiments, the processing device 140 may generate one or more reconstruction images based on the original images. The reconstruction image may include a multiplanar reconstruction (MPR) image, a curved planar reconstruction (CPR) image, a three-dimensional (3D) rendering image, or the like. In some embodiments, the processing device 140 may input the original images and the reconstruction images into the fracture detection model to detect the bone fracture regions in the original images and the reconstruction images, and display the fracture detection results in the original images and the reconstruction images, respectively. In some embodiments, the processing device 140 may input the original images into the fracture detection model to detect the bone fracture regions in the original images. The processing device 140 may display the fracture detection result of the original images in the reconstruction image. For example, the processing device 140 may display a marker of a bone fracture region at a location of a CPR image corresponding to the detected bone fracture region in the original images. As another example, the processing device 140 may display a marker of the combined bone fracture region in a 3D rendering image.

Figure 5B:
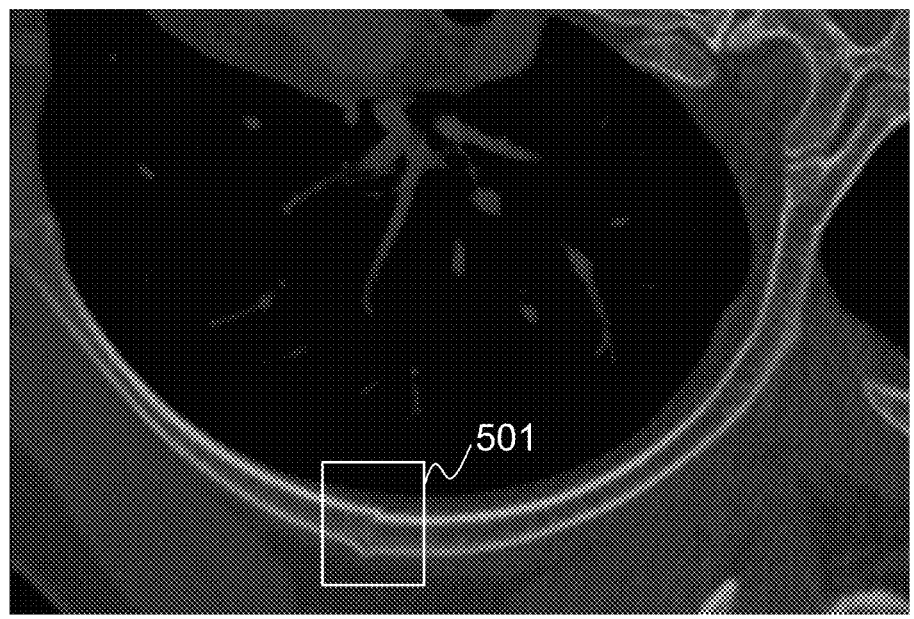
FIGS. 5B-5C are schematic diagrams illustrating examples of displaying a marker of a bone fracture region according to some embodiments of the present disclosure.
Figure 5C:
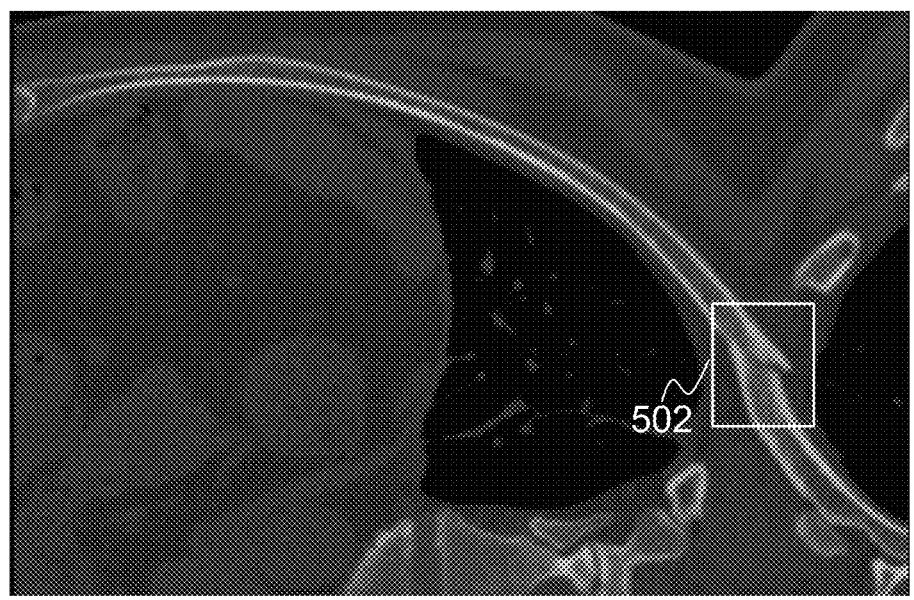

Merely by way of example, FIGS. 5B-5C are schematic diagrams illustrating examples of displaying a marker of a bone fracture region according to some embodiments of the present disclosure. FIG. 5B shows a stretched CPR image of a rib. The rib is on the right side of the human body and is the third rid along the direction from the head to the feet. A marker of rectangle frame 501 may be displayed in the CRP image to mark the bone fracture region of the rib. FIG. 5C shows a stretched CPR image of a rib. The rib is on the left side of the human body and is the eighth rid along the direction from the head to the feet. A marker of rectangle frame 502 may be displayed in the CRP image to mark the bone fracture region of the rib.

In some embodiments, the processing device 140 may display the original image, the target image, and the reconstruction image (e.g., the MPR image, the CPR image, the 3D rendering image, etc.) of the rib at the same time.

In existing processes for fracture detection, doctors may analyze a plurality of medical images and use their own experience to detect bone fractures. Compared with the existing processes for fracture detection, the present disclosure provides methods and/or systems for fracture detection to achieve automated detection using a fracture detection model without or with minimal reliance on a doctor's experience in specific cases, which may reduce manual operations and the time to proform the fracture detection, improve the efficiency and the accuracy of fracture detection, and/or obtain a more objective fracture detection result.

In some embodiments, the processing device 140 may detect two or more bone fracture regions of the one or more ribs in a medical image using the fracture detection model described in the present disclosure. For example, the processing device 140 may detect two or more bone fracture regions in different ribs in a medical image using the fracture detection model. As another example, the processing device 140 may detect two or more bone fracture regions in a same rib in a medical image using the fracture detection model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may combine the detected fracture regions whose distance between each other that is equal to the distance threshold. As another example, the processing device 140 may detect a bone fracture region of the one or more ribs in the medical image using the fracture detection model.

Figure 7A:
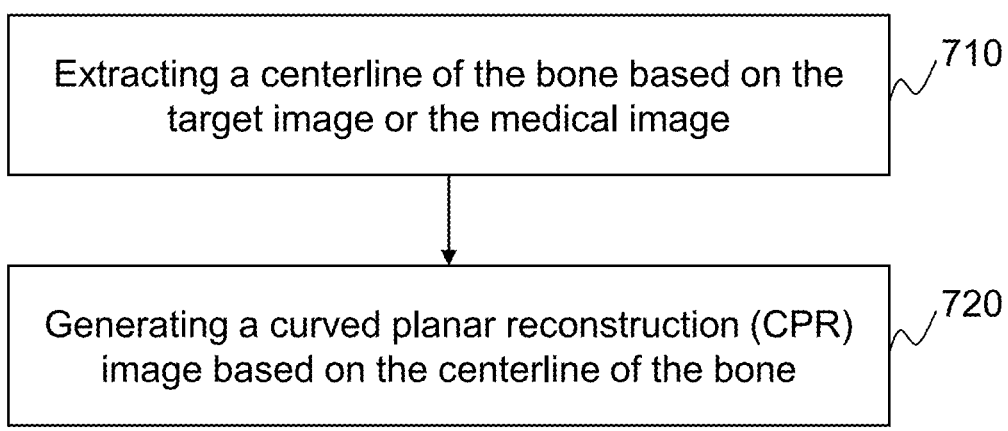
FIG. 7A is a flowchart illustrating an exemplary process for generating a curved planar reconstruction (CPR) image according to some embodiments of the present disclosure.

FIG. 7A is a flowchart illustrating an exemplary process for generating a CPR image according to some embodiments of the present disclosure. In some embodiments, the process 700 may be implemented in the computer aided diagnosis system 100 illustrated in FIG. 1. For example, the process 700 may be stored in a storage medium (e.g., the storage device 150, or the storage 220 of the processing device 140) in the form of instructions, and can be invoked and/or executed by the processing device 140 (e.g., the processor 210 of the processing device 140, or one or more modules in the processing device 140 illustrated in FIG. 4). The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In the present disclosure, a process for automatically extracting a centerline of ribs may be used to generate the CPR image.

In 710, the processing device 140 (e.g., the processing module 430) may extract a centerline of the ribs based on the target image or the medical image. In some embodiments, the series of 2D original images may be stacked together to generate volume data of the ROI including the ribs. Doctors need to manually determine a plurality of points in the ribs in the volume data. The processing device 140 may determine the centerline based on the manually determined points.

In some embodiments, a process for automatically extracting a centerline of ribs may be used to generate the CPR image. The processing device 140 may use any existing technology for automated centerline extraction, such as a topological thinning algorithm, an algorithm based on distance transform and shortest path, a tracking-based algorithm, or the like, or any combination thereof.

For example, in the topological thinning algorithm, border pixels (or voxels) of the bone in the target image or the medical image may be symmetrically peeled conforming to topology principles in an iterative process until no pixel (or voxel) reduction occurs. The topological thinning algorithm may generate a one-pixel (or voxel) wide centerline region of the bone directly with exact centrality. Border points whose deletion do not induce any topological property change may be peeled iteratively.

As another example, in the tracking-based algorithm, an initial point and direction may be determined in the target image or the medical image. After that, the centerline path may grow in a search direction iteratively based on local properties, such as the spatial continuity of the bone's centerline points, curvature, diameter, and intensity of the bone.

As still another example, in the algorithm based on distance transform and shortest path, an initial point may be determined in the target image or the medical image. The distance transform may be performed on the target image or the medical image by determining a distance between each pixel (or voxel) in the target image or the medical image and the initial point. Pixels (or voxels) with a same distance away from the initial point may be included a same group. In each group, pixels (or voxels) with a shortest distance away from the surface of the bone and a largest pixel value (or voxel value) may be identified. The centerline of the bone may be determined by connecting the identified pixels (or voxels).

In 720, the processing device 140 (e.g., the processing module 430) may generate a curved planar reconstruction (CPR) image based on the centerline of the ribs.

Figure 7B:
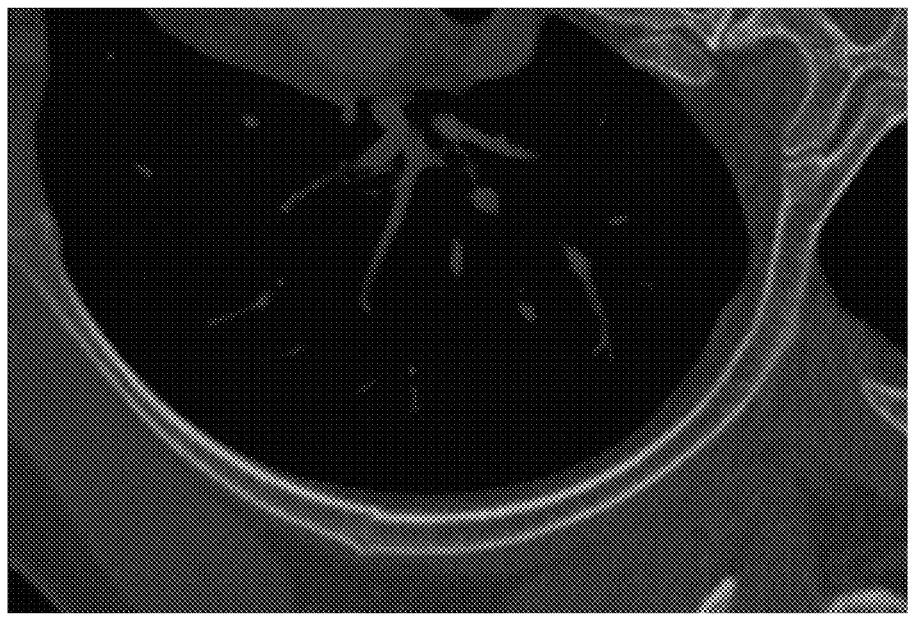
FIGS. 7B-7C are schematic diagrams illustrating examples of stretched CPR images of a rib according to some embodiments of the present disclosure.
Figure 7C:

In some embodiments, because of the morphology of the rib, the processing device 140 may generate a stretched CPR image of the rib. In the stretched CPR image of the rib, the rib may be displayed from a view parallel to the rib (e.g., along the extending direction of the rib), which may make doctors easily observe the entire and real morphology of the rib in the CPR image. For example, FIG. 7B shows a stretched CPR image of a rib. The rib is on the right side of the human body and is the third rid along the direction from head to feet. FIG. 7C shows a stretched CPR image of a rib. The rib is on the left side of the human body and is the eighth rid along the direction from head to feet.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 8:
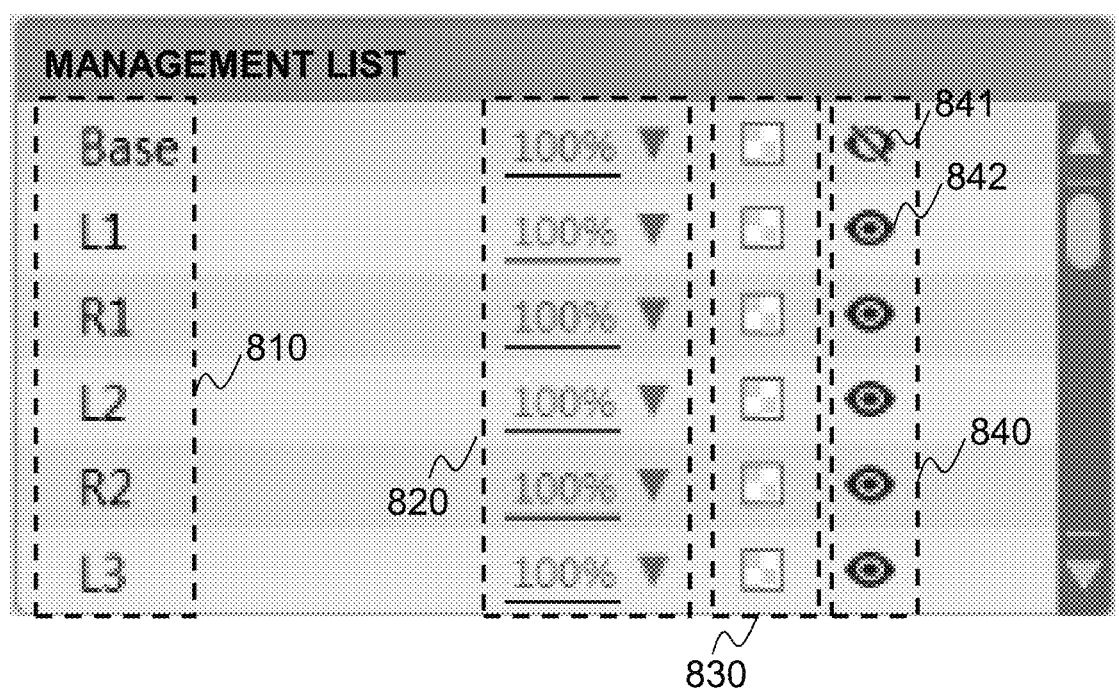
FIG. 8 is a schematic diagram illustrating an example of a management list according to some embodiments of the present disclosure.

FIG. 8 is a schematic diagram illustrating an example of a management list according to some embodiments of the present disclosure. In some embodiments, the processing device 140 may generate a management list to manage images (e.g., the original images, the target images, and/or the reconstruction images) of the ribs, the fracture detection result, one or more bone masks of the ribs, and/or the result of centerline extraction.

In some embodiments, there may be a mapping relationship between the management list and the images of ribs or the fracture detection result.

For example, the management list may include a menu including a number of at least one rib, a name of at least one image of the ribs, a name of other kinds of bones, and function options. For example, as shown in FIG. 8, the list 800 is presented on an interactive interface, displayed in the processing device 140 through, for example, the I/O 230, of a part of a management list. In the list 800, the numbering of several ribs are listed in column 810. In some embodiments, the ribs are divided into two sections by the spine, e.g., a right section located on the right side of the human body and a left section located on the left side of the human body. Along a direction from the head to feet of the human body, the ribs in each section are numbered from 1 and increase. For example, the rib that is in the right section and is closest to the head has a number of R1. The rib that is in the left section and is closest to the head has a number of L1. In the column 810, "Base" refers to the bones (e.g., the spine) other than the ribs in the images of ribs.

In the list 800, function options are listed in columns 820-840. Options of the transparent of the displayed ribs are listed in the column 820. Options of the color of the displayed ribs are listed in the column 830. Options as to whether to display a specific rib are listed in the column 840. For example, the sign 841 indicates that the bones (e.g., the spine) other than the ribs are not displayed in all of or a portion of the images of ribs. As another example, the sign 842 indicates that the rib L1 is displayed in the images of ribs.

Figure 9A:
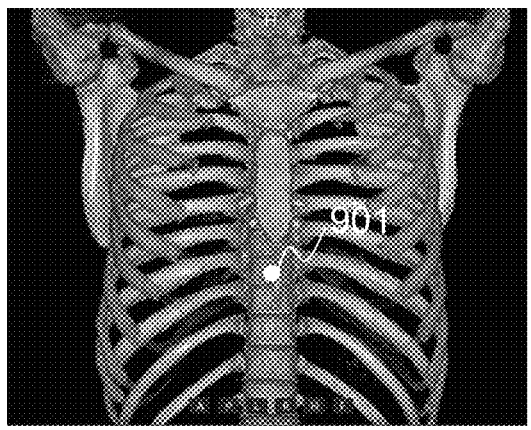
FIGS. 9A-9D are schematic diagrams illustrating examples of different images of ribs according to some embodiments of the present disclosure.
Figure 9B:
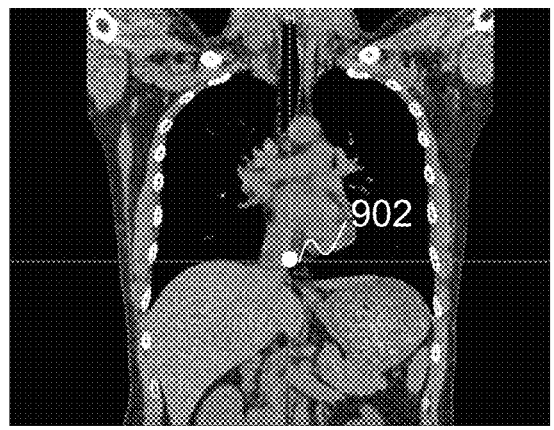
Figure 9C:
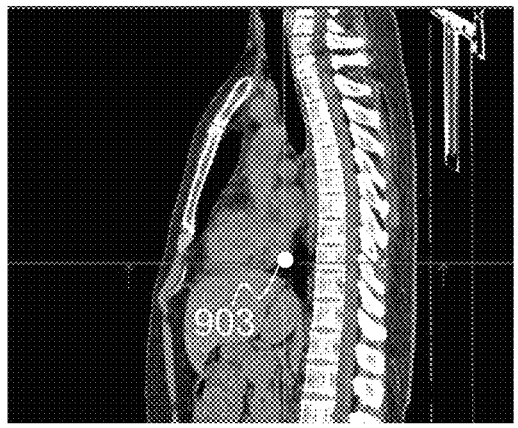
Figure 9D:
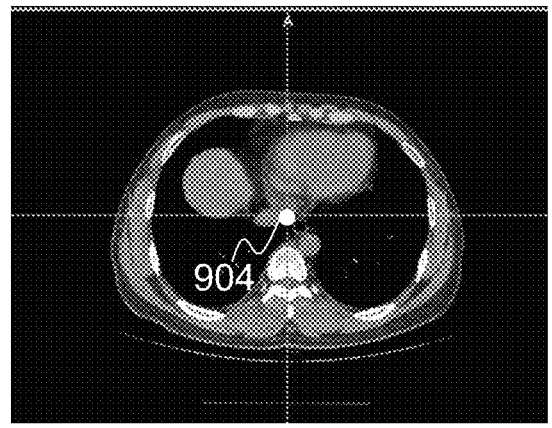

Merely by way of example, when a doctor clicks the numbering of a rib in the management list, images (e.g., the original image, the target image, and the reconstruction image) including the rib may be displayed. The rib in the images may be marked. The fracture detection result may be displayed in the images of the rib. For example, when a doctor clicks "L1" in the management list 800 or clicks the rib L1 in a 3D rendering image (e.g., FIG. 9A), a stretched CPR image and/or one or more MPR images including the rib L1 may be displayed. The fracture detection result may be displayed in the stretched CPR image and/or one or more MPR images including the rib L1.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the computer aided diagnosis system 100 may enable doctors to observe the rib structure and/or the bone fracture of the ribs from different angles of view through different images of ribs at the same time. In some embodiments, the processing device 140 may locate the images of ribs into a same spatial coordinate system so that locations in the images of ribs have a corresponding relationship. The processing device 110 may receive an instruction of selecting, for display, a first location in a first medical image of multiple medical images. The processing device 110 may simultaneously display the first medical image, or a portion thereof, including the selected first location and a second medical image, or a portion thereof, of the multiple medical images. The second medical image may include a second location corresponding to the first location. The processing device 110 may display a marker of the second location in the second medical image.

For example, FIGS. 9A-9D are images corresponding to different angles of view of an ROI including ribs. If a doctor selects location 901 (e.g., the doctor puts a cursor in location 901) in FIG. 9A, locations 902-904 in FIGS. 9B-9C corresponding to location 901 may be marked at the same time (e.g., the cursors in FIGS. 9B-9C may be automatically located in locations 902-904 at the same time).

EXAMPLES

For further understanding the present disclosure, several examples are given below, but the examples do not limit the scope of the present disclosure.

Example 1

Figure 10:
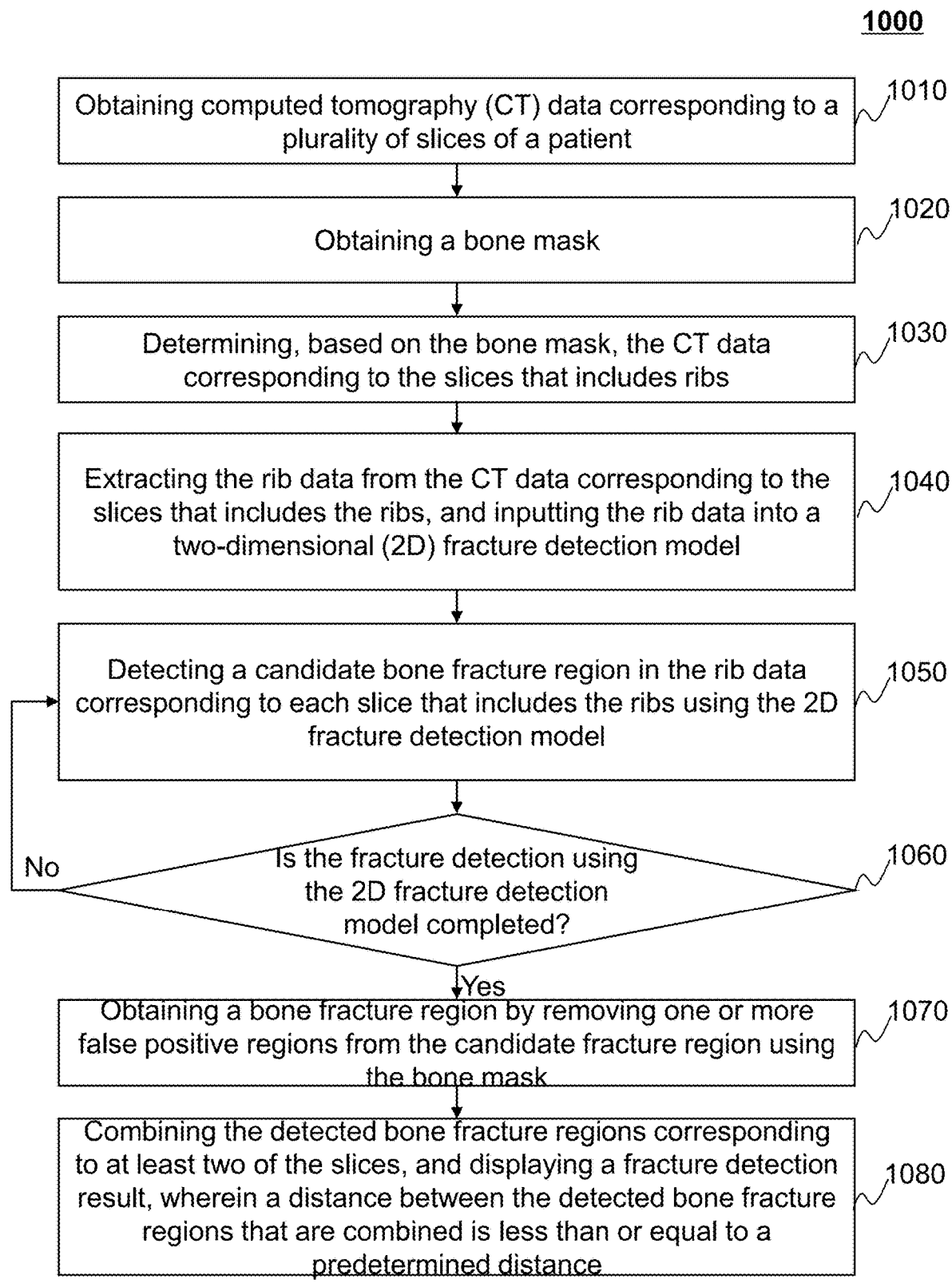
FIGS. 10-12 are flowcharts illustrating exemplary processes for detecting bone fracture according to some embodiments of the present disclosure.

FIG. 10 is a flowchart illustrating an exemplary process 1000 for detecting bone fracture according to some embodiments of the present disclosure. In the embodiments, the fracture detection model is a 2D fracture detection model.

In 1010, the processing device 140 may obtain computed tomography (CT) data of ribs corresponding to a plurality of slices of a patient (e.g., a series of 2D original images taken at successive slices of the patient).

In 1020, the processing device 140 may obtain a bone mask (e.g., a 3D bone mask) of the ribs.

In 1030, the processing device 140 may determine, based on the bone mask, the CT data (e.g., the 2D original images) corresponding to the slices that include the ribs.

In 1040, the processing device 140 may extract the rib data (e.g., the target images) from the CT data corresponding to the slices that include the ribs, and input the rib data into a two-dimensional (2D) fracture detection model.

In 1050, the processing device 140 may detect a candidate bone fracture region in the rib data corresponding to each slice that includes the ribs using the 2D fracture detection model.

In 1060, the processing device 140 may determine whether the fracture detection using the 2D fracture detection model is completed. In response to a determination that the fracture detection using the 2D fracture detection model is not completed, the process 1000 may proceed to operation 1050. In response to a determination that the fracture detection using the 2D fracture detection model is completed, the process 1000 may proceed to operation 1070.

In 1070, the processing device 140 may obtain a bone fracture region by removing one or more false positive regions from the candidate fracture region using the bone mask.

In 1080, the processing device 140 may combine the detected bone fracture regions corresponding to at least two of the slices, and display a fracture detection result. A distance between the detected bone fracture regions that are combined may be less than or equal to a predetermined distance.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 1040 may be omitted. The processing device 140 may detect a candidate bone fracture region in the CT data (e.g., the 2D original images) corresponding to the slices that include the ribs.

Example 2

Figure 11:
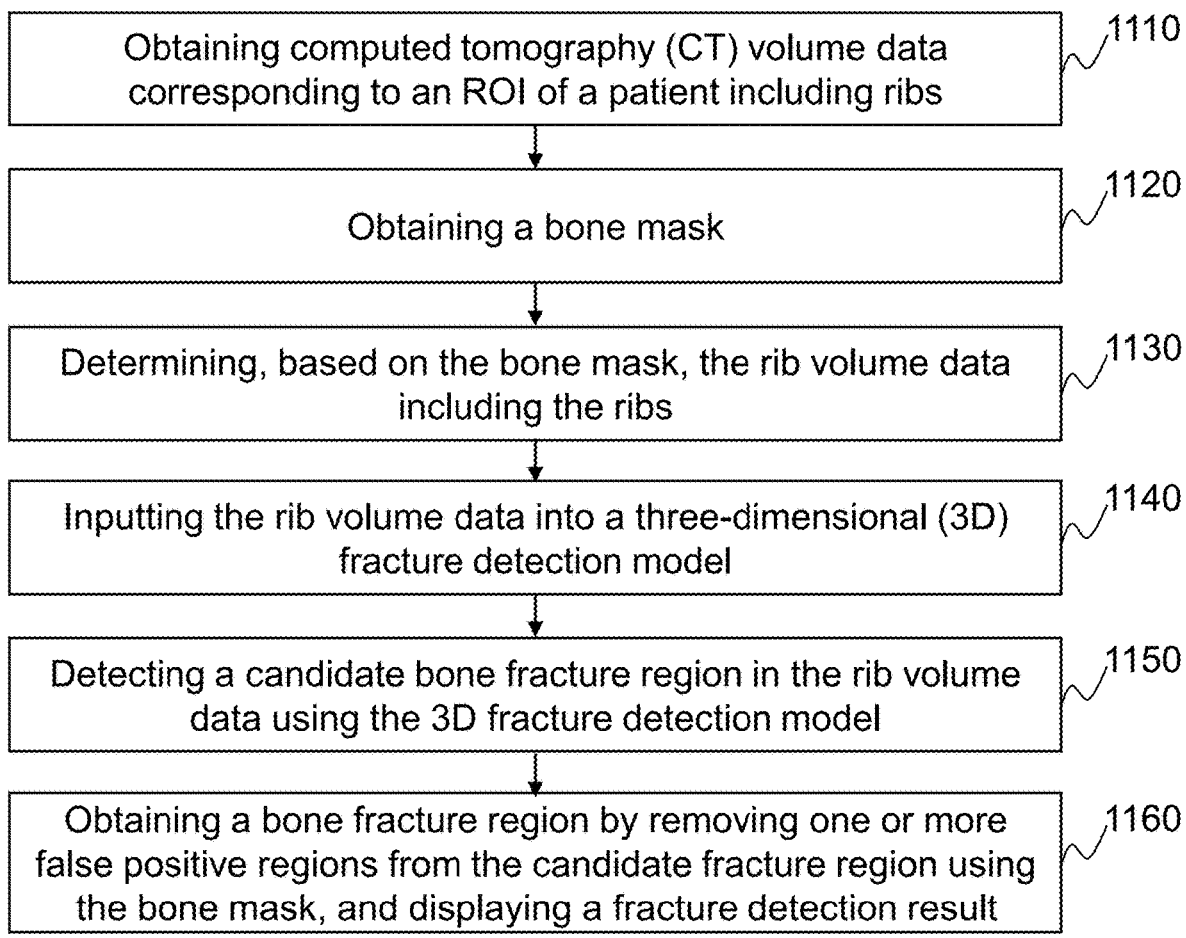

FIG. 11 is a flowchart illustrating an exemplary process 1100 for detecting bone fracture according to some embodiments of the present disclosure. In the embodiments, the fracture detection model is a 3D fracture detection model.

In 1110, the processing device 140 may obtain computed tomography (CT) volume data corresponding to an ROI of a patient including ribs.

In 1120, the processing device 140 may obtain a bone mask (e.g., a 3D bone mask) of the ribs.

In 1130, the processing device 140 may determine, based on the bone mask, the rib volume data (e.g., corresponding to a volume smaller than that corresponding to the CT volume data) including the ribs.

In 1140, the processing device 140 may input the rib volume data into a three-dimensional (3D) fracture detection model.

In 1150, the processing device 140 may detect a candidate bone fracture region in the rib volume data using the 3D fracture detection model.

In 1160, the processing device 140 may obtain a bone fracture region by removing one or more false positive regions from the candidate fracture region using the bone mask, and display a fracture detection result.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Example 3

Figure 12:
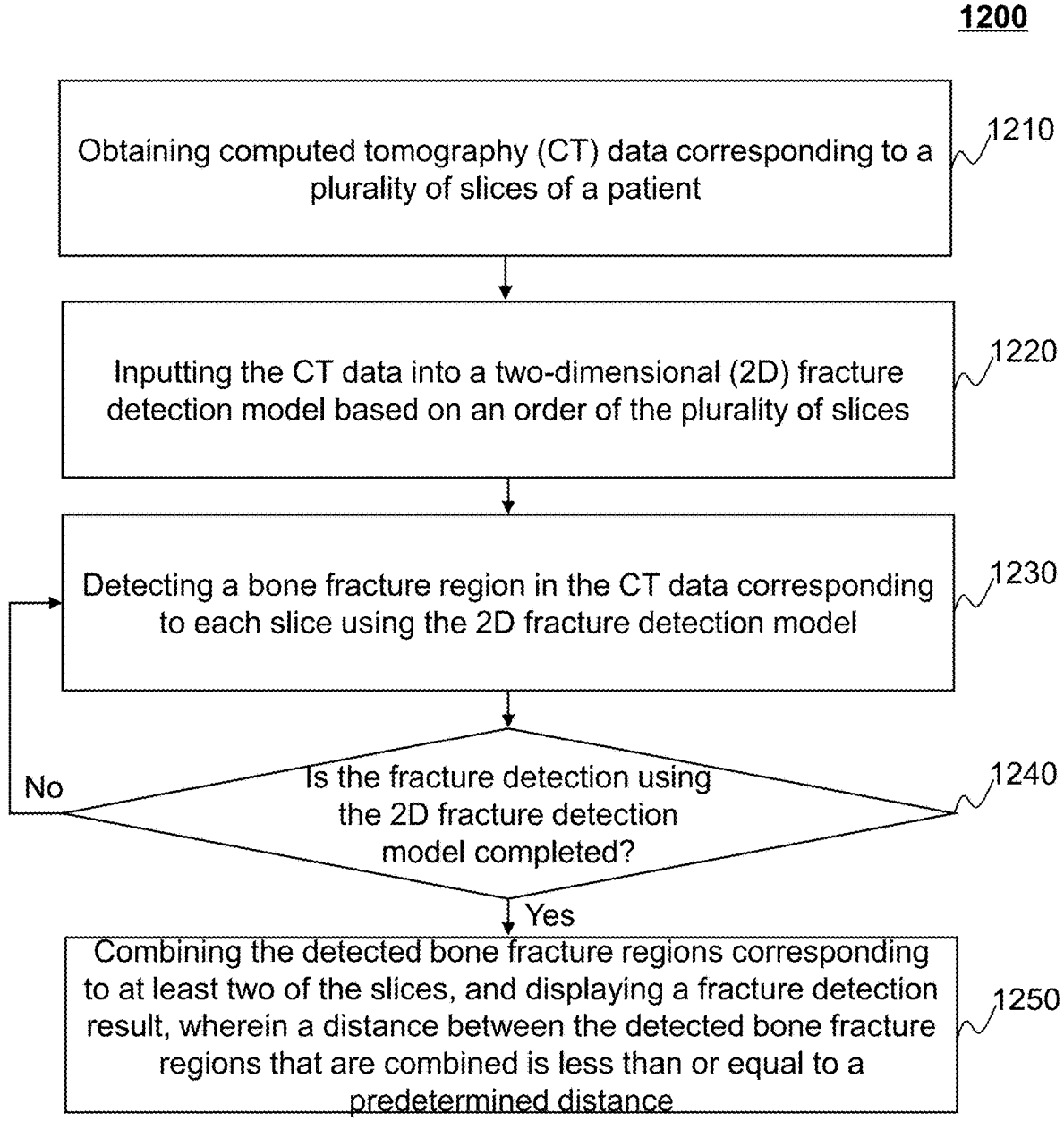

FIG. 12 is a flowchart illustrating an exemplary process 1200 for detecting bone fracture according to some embodiments of the present disclosure. In the embodiments, the fracture detection model is a 2D fracture detection model, and the fracture detection model has functions of fracture detection and bone segmentation.

In 1210, the processing device 140 may obtain computed tomography (CT) data of ribs corresponding to a plurality of slices of a patient (e.g., a series of 2D original images taken at successive slices of the patient).

In 1220, the processing device 140 may input the CT data into a two-dimensional (2D) fracture detection model based on an order of the plurality of slices.

In 1230, the processing device 140 may detect a bone fracture region in the CT data corresponding to each slice that includes the ribs using the 2D fracture detection model.

In 1240, the processing device 140 may determine whether the fracture detection using the 2D fracture detection model is completed. In response to a determination that the fracture detection using the 2D fracture detection model is not completed, the process 1200 may proceed to operation 1230. In response to a determination that the fracture detection using the 2D fracture detection model is completed, the process 1200 may proceed to operation 1250.

In 1250, the processing device 140 may combine the detected bone fracture regions corresponding to at least two of the slices, and display a fracture detection result. A distance between the detected bone fracture regions that are combined may be less than or equal to a predetermined distance.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:

1. A computer-aided diagnosis method for detecting bone fracture implemented on a computing device having one or more processors and one or more storage devices, the method comprising:
   obtaining one or more medical images related to one or more bones, wherein the one or more medical images include multiple medical images;
   obtaining a fracture detection model generated based on a machine learning model;
   for at least one of the one or more medical images, detecting one or more bone fracture regions of the one or more bones in the medical image using the fracture detection model;
   receiving an instruction of selecting, for display, a first location in a first medical image of the one or more medical images; and
   simultaneously displaying the first medical image, or a portion thereof, including the selected first location and a second medical image, or a portion thereof, of the one or more medical images, the second medical image including a second location corresponding to the first location.

2. The method of claim 1, further comprising:
   reconstructing one or more bone images based on the one or more detected bone fracture regions; and
   displaying a marker of the one or more detected bone fracture regions in the one or more bone images or the one or more medical images.

3. The method of claim 2, wherein the one or more bone images include at least one of a stretched curved planar reconstruction (CPR) image, a multiplanar reconstruction (MPR) image, and a three-dimensional (3D) rendering image.

4. The method of claim 1, further comprising:
   displaying a management list for managing at least one of one or more bone masks related to the one or more bones and information related to the one or more detected bone fracture regions;
   receiving an instruction related to selecting at least one of the one or more bones, the instruction being generated through the management list or the 3D rendering image; and
   displaying at least one of the stretched CPR image and one or more MPR images related to the at least one selected bone based on the instruction.

5. The method of claim 1, wherein the displaying of the second medical image, or a portion thereof, includes displaying a marker of the second location.

6. A computer-aided diagnosis system for detecting bone fracture, comprising:
   at least one storage device including a set of instructions;

at least one processor in communication with the at least one storage device, wherein when executing the set of instructions, the at least one processor is directed to cause the system to perform operations including:
  obtaining one or more medical images related to one or more bones, wherein the one or more medical images include multiple medical images;
  obtaining a fracture detection model generated based on a machine learning model;
  for at least one of the one or more medical images, detecting one or more bone fracture regions of the one or more bones in the medical image using the fracture detection model;
  receiving an instruction of selecting, for display, a first location in a first medical image of the one or more medical images; and
  simultaneously displaying the first medical image, or a portion thereof, including the selected first location and a second medical image, or a portion thereof, of the one or more medical images, the second medical image including a second location corresponding to the first location.

7. The system of claim 6, wherein the fracture detection model is obtained by performing operations including:
  obtaining training images in which bone fractures are marked; and
  determining the fracture detection model by training a preliminary model using the training images.

8. The system of claim 6, wherein the detecting the one or more bone fracture regions of the one or more bones in the medical image using the fracture detection model including:
  detecting one or more candidate fracture regions in the medical image using the fracture detection model; and
  obtaining the one or more bone fracture regions by removing one or more false positive regions from the one or more candidate fracture regions using a bone mask related to the one or more bones.

9. The system of claim 6, wherein when executing the set of instructions, the at least one processor is directed to cause the system to perform additional operations including:
  displaying a marker of the one or more bone fracture regions in the at least one of the one or more medical images.

10. The system of claim 6, wherein when executing the set of instructions, the at least one processor is directed to cause the system to perform additional operations including:
  determining a type of bone fracture in the one or more bone fracture regions using the fracture detection model.

11. The system of claim 6, wherein the one or more medical images include multiple medical images taken at different slices of the one or more bones, and the at least one processor is directed to cause the system to perform additional operations including:
  determining whether there are at least two of the multiple medical images in each of which the one or more bone fracture regions are detected;
  determining a distance between the detected bone fracture regions in the at least two of the multiple medical images in response to a determination that there are at least two of the multiple medical images in each of which the one or more bone fracture regions are detected;
  determining whether the distance is less than a distance threshold; and
  combining the detected bone fracture regions in the at least two of the multiple medical images in response to a determination that the distance is less than the distance threshold, the detected bone fracture regions in the at least two of the multiple medical images being deemed to relate to a same bone fracture.

12. The system of claim 11, wherein when executing the set of instructions, the at least one processor is directed to cause the system to perform additional operations including:
  reconstructing one or more bone images based on the one or more detected bone fracture regions or the combined bone fracture region; and
  displaying a marker of the one or more detected bone fracture regions or the combined bone fracture region in the one or more bone images.

13. The system of claim 12, wherein the one or more bone images include at least one of a curved planar reconstruction (CPR) image, a multiplanar reconstruction (MPR) image, and a three-dimensional (3D) rendering image.

14. The system of claim 6, wherein when executing the set of instructions, the at least one processor is directed to cause the system to perform additional operations including:
  extracting a centerline of at least one of the one or more bones based on the one or more medical images; and
  generating a stretched CPR image based on the centerline of the bone.

15. The system of claim 14, wherein when executing the set of instructions, the at least one processor is directed to cause the system to perform additional operations including:
  displaying a management list for managing at least one of one or more bone masks related to the one or more bones and information related to the one or more detected bone fracture regions.

16. The system of claim 15, wherein when executing the set of instructions, the at least one processor is directed to cause the system to perform additional operations including:
  receiving an instruction related to selecting at least one of the one or more bones, the instruction being generated through the management list or the 3D rendering image; and
  displaying at least one of the stretched CPR image and one or more MPR images related to the at least one selected bone based on the instruction.

17. The system of claim 6, wherein the fracture detection model is obtained based on a convolutional neural network (CNN).

18. The system of claim 6, wherein the displaying of the second medical image, or a portion thereof, includes displaying a marker of the second location.

19. The system of claim 6, wherein when executing the set of instructions, the at least one processor is directed to cause the system to perform operations including:
  for at least one of the one or more medical images, generating a target image including the one or more bones by segmenting the one or more bones from the medical image.

20. A non-transitory computer readable medium, comprising at least one set of instructions for detecting bone fracture, wherein when executed by one or more processors of a computing device, the at least one set of instructions causes the computing device to perform a method, the method comprising:
  obtaining one or more medical images related to one or more bones, wherein the one or more medical images include multiple medical images;
  obtaining a fracture detection model generated based on a machine learning model;

for at least one of the one or more medical images, detecting one or more bone fracture regions of the one or more bones in the medical image using the fracture detection model;

receiving an instruction of selecting, for display, a first location in a first medical image of the one or more medical images; and simultaneously displaying the first medical image, or a portion thereof, including the selected first location and a second medical image, or a portion thereof, of the one or more medical images, the second medical image including a second location corresponding to the first location.

\* \* \* \* \*